(12) United States Patent
Bartov

(10) Patent No.: US 7,243,331 B2
(45) Date of Patent: Jul. 10, 2007

(54) METHOD AND SYSTEM FOR CONTROLLING THE QUALITY OF A RETICLE

(75) Inventor: Avishay Bartov, Hod-Hasharon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 340 days.

(21) Appl. No.: 10/767,358

(22) Filed: Jan. 28, 2004

(65) Prior Publication Data

US 2005/0166171 A1 Jul. 28, 2005

(51) Int. Cl.
*G06F 17/50* (2006.01)
*G06K 9/00* (2006.01)
*G01N 21/00* (2006.01)

(52) U.S. Cl. ............... 716/19; 382/144; 356/237.4
(58) Field of Classification Search ............ 716/19–21; 356/257.1, 237.3–237.5; 430/54; 382/144–145; 700/121, 109–110
See application file for complete search history.

(56) References Cited

U.S. PATENT DOCUMENTS

| | | | |
|---|---|---|---|
| 6,268,093 B1 * | 7/2001 | Kenan et al. ............... | 430/30 |
| 6,376,264 B1 * | 4/2002 | Englisch ...................... | 438/14 |
| 6,466,314 B1 * | 10/2002 | Lehman ...................... | 356/237.1 |
| 6,614,520 B1 * | 9/2003 | Bareket et al. ............ | 356/237.3 |
| 2002/0164064 A1 * | 11/2002 | Karklin et al. ............... | 382/145 |
| 2003/0048939 A1 * | 3/2003 | Lehman ........................ | 382/144 |
| 2004/0066963 A1 * | 4/2004 | Hechtl et al. ................ | 382/144 |

OTHER PUBLICATIONS

Search Report, "International Searching Authority", PCT/US2005/001748, (Apr. 13, 2005), 13 pgs.
Tomlinson, Wanda, et al., "Cost Effective Reticle Quality Management Strategies in Wafer Fabs", *IEEE/SEMI* Boxton, MA, (Sep. 8, 1999), pp. 254-258.

\* cited by examiner

*Primary Examiner*—Stacy A Whitmore
(74) *Attorney, Agent, or Firm*—Tarek N. Fahmi

(57) ABSTRACT

A method and system are presented for use in controlling the quality of a reticle. The method includes processing and analyzing reference data and test data, and generating output data indicative of the current condition of the reticle. The reference data is indicative of at least a portion of a reference pattern, which is produced on a reference article by using said reticle, when in a satisfied condition. The test data is indicative of a test pattern produced on an identical article using said reticle when in the current condition, a certain time period after said reticle has been in use or stored.

33 Claims, 3 Drawing Sheets

Data sets $MD_1$ (printed reference pattern) & $MD_2$ (printed test pattern) processed and analyzed Output indicative of reticle condition provided

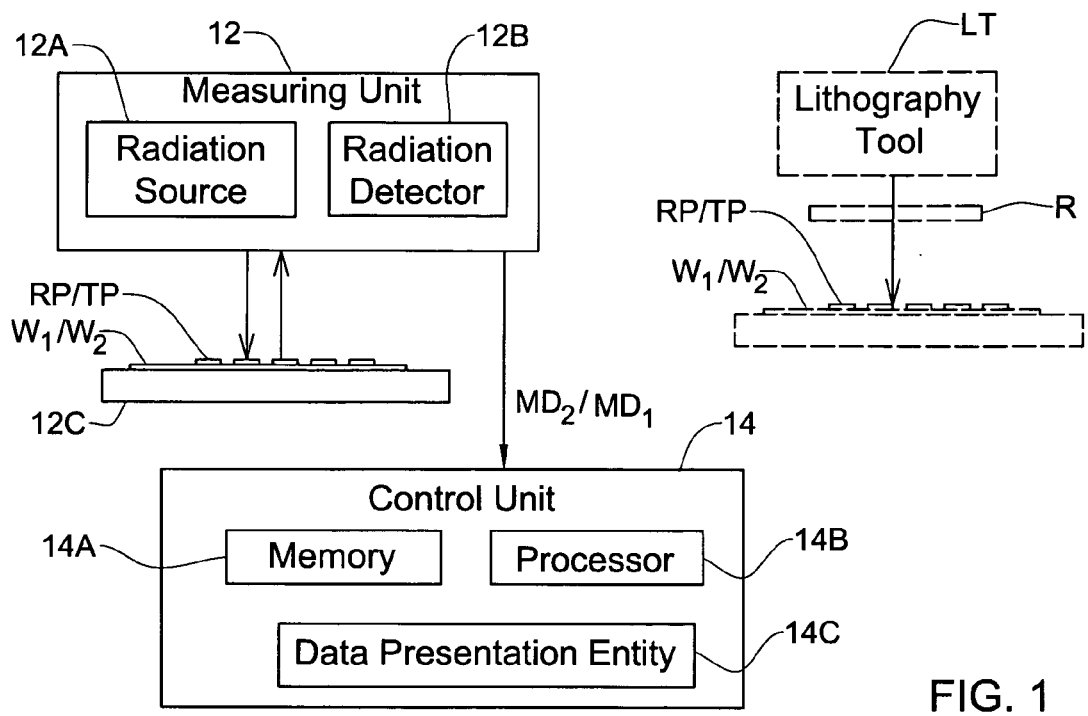
FIG. 1
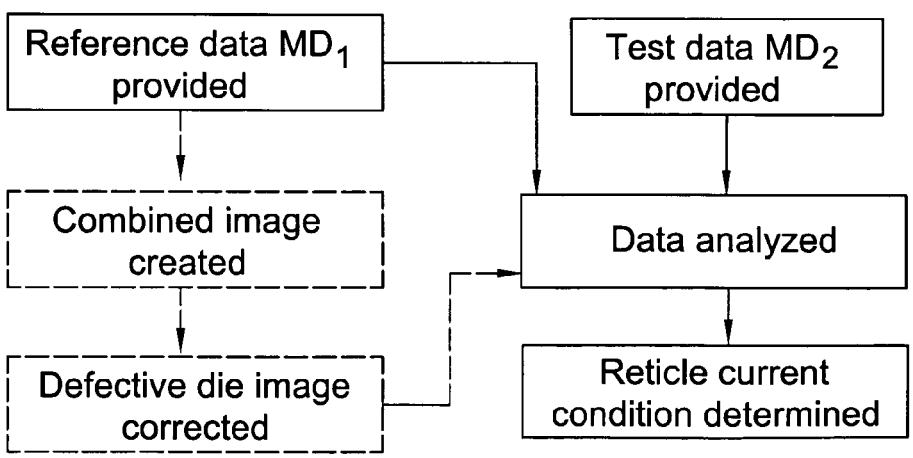
FIG. 2A
FIG. 2B

METHOD AND SYSTEM FOR CONTROLLING THE QUALITY OF A RETICLE

FIELD OF THE INVENTION

This invention is generally in the field of inspection techniques, and relates to a method and system for controlling reticles or masks that are used in fabricating patterned structures, such as microelectronic devices, by means of a microphotolithographic process.

BACKGROUND OF THE INVENTION

Reticles are used with photolithography tools (i.e., "steppers") in the manufacture of semiconductor devices. Photolithography is one of the principle processes in the manufacture of semiconductor devices, and consists of patterning the surface of a semiconductor wafer in accordance with the active elements of the semiconductor devices to be produced. This is a layer-by-layer methodology, with each layer's manufacture including various deposition and etching processes, which are applied using a reticle. The reticle is stepped sequentially over the wafer and at each step the pattern of the reticle is transferred to the wafer, resulting in a complete layout on the wafer. To produce an operational microelectronic circuit, a reticle must be as defect-free as possible. Usually, the FAB engineers assume that the reticle has been tested in the reticle shop and is logically correct. Along the reticle life time in the production line, there is a need for the periodic inspection of the reticle's current condition to detect various defects therein that could potentially reduce the microelectronic circuit fabrication yields.

Various techniques for the reticle inspection have been developed. For example, it is known to detect defects such as the existence of foreign particles on the surface of a reticle, by utilizing the so-called "dark-field" inspection. According to this technique light that returns from the illuminated surface of the reticle at azimuth and elevation different from those where the most specular reflection occurs, is collected. This collected light is thus mainly formed by light components scattered from the foreign particles existing on the surface of the reticle.

U.S. Pat. No. 6,268,093, assigned to the assignee of the present application, discloses a method for reticle inspection using aerial imaging. According to this technique, defects such as line width errors in the printed image and surface defects can be detected. The line width errors are detected on the die area. Detection is performed by acquiring the image of the reticle under the same optical conditions as the exposure conditions (i.e. wavelength, numerical aperture, sigma, and illumination aperture type) and by comparing multiple dies to find errors in the line width. Surface defects are detected all over the reticle. The detection of surface defects is performed by acquiring transmission and dark-field reflection images of the reticle and using the combined information to detect particles, and other surface defects.

U.S. Pat. No. 6,466,314, assigned to the assignee of the present application, discloses a reticle inspection system and method. This technique consists of the following: A test reticle is generated comprising a plurality of test pattern-features thereon. Then, a wafer is manufactured using this test reticle, and a transfer of at least one of the plurality of pattern features from this reticle to the wafer is determined.

U.S. Pat. No. 6,614,520 discloses a method for inspecting a reticle for defects that occur over time. This technique utilizes generating and storing a "baseline" image of the reticle and then periodically generating a "current" image of the reticle and comparing the current and baseline images. The baseline image is taken at a time when the reticle is known to be acceptable. This may be when the reticle has been "qualified" by an optical test or when a die fabricated by reticle has passed an electrical test.

SUMMARY OF THE INVENTION

There is a need in the art to facilitate reticle inspection by providing a novel method and system enabling direct determination of the actual printing defects of the reticle.

One of the problems with the conventional reticle inspection techniques is associated with the following: According to the conventional techniques, the reticle is scanned to identify irregularities in the transmission/reflection ratios of the reticle surface. However, not every irregularity identified from the optical response of a reticle prints a defect on a wafer, while only those irregularities of the reticle that defect the wafer produced by this reticle are to be controlled. In this connection, it is important to note that the reticle itself is the end product of a complicated design process in which the entire layout of the wafer is determined and tolerances are set for the manufacture process. Nevertheless, it is often the case that the final manufactured wafer deviates from the design of the reticle. The reasons for the wafer being different from the design of the reticle may include defects in the reticle manufacture and unexpected interactions between the reticle design and the process used manufacturing the wafers. Therefore, reticles are typically inspected both by the mask shop manufacturer and at the semiconductor fabrication plant (FAB). According to current practice, reticles having non-repairable defects thereon are not shipped by the mask shop or are returned by the FAB, and never used. Due to the rapid reduction in design rules (the smallest resolvable feature size), the manufacture of reticles is expected to become more difficult, and the price of reticles is expected to rise. Therefore, it will become more desirable to use a reticle even if it is defective, providing however, that its defects do not invalidate the manufactured wafer.

Another problem is associated with the conventional wafer inspection methods involving comparing adjacent dies on the wafer, the so-called "Die-to-Die" inspection scheme, which is based on subtracting the scanned image of adjacent dies and threshold the result in order to allow a reasonable false defects rate. The Die-to-Die method assumes a very low probability of having a defect on the same position in two adjacent dies. In case the reticle used for printing a wafer includes only one die, a defect on the reticle would be printed on every chip on the wafer, and the die-to-die based inspection tool would not be able to find this kind of defect.

The present invention solves the above problems by providing a novel system and method for controlling the quality of a reticle. The main idea of the present invention consists of directly detecting printing defects caused by a reticle itself, by periodically (generally, when needed) inspecting the results of printing on a structure (e.g., wafer) using this reticle. The inspected printing result is in the form of a response of the printed pattern on the structure to predetermined incident radiation (e.g., an image of the pattern). The inspection includes comparing between reference and test data.

The use of the following terms in the description of the invention should be clarified:

The term "reference data set" or "reference measured data set" used herein signifies data indicative of at least a portion of a pattern produced (printed) using a reticle when considered to be of a satisfied condition (i.e., satisfied quality), the so-called "brand new reticle" or "perfect reticle".

The term "test data set" or "test measured data set" used herein signifies data indicative of at least a portion of a test pattern produced (printed) using said reticle after said reticle has been in use or has been stored for a certain period of time.

Generally, the term "data indicative of a pattern" or "data indicative of at least a portion of a pattern" means data indicative of a radiation response of a pattern to predetermined incident radiation, which may be data indicative of an image of the pattern. For the simplicity of explanation of the main principles of the invention, this term is at times replaced by the term "data indicative of an image of a pattern", but it should be understood that it is not necessarily the image of the entire patterned area and not necessarily an image as such, but may, for example, include optical critical dimension scatterometric data, and is not necessarily obtained by optical means, but may for example be obtained by the charged particle beam inspection (e.g., scanning electron microscopy).

The term "article" signifies a single- or multi-layer structure, for example such as a semiconductor wafer structure, which may be a single-layer structure (the so-called "bare wafer") or a multi-layer stack.

Thus, according to one broad aspect of the present invention, there is provided, a method of controlling the current condition of a reticle, the method comprising: processing and analyzing test data indicative of a test pattern produced on an article using the reticle when in the current condition, and reference data indicative of a reference pattern previously produced on the same or another identical article using said reticle when considered to be of a satisfied condition, and generating output data indicative of the current condition of said reticle.

Preferably, the data analysis includes processing at least one of the reference and test data sets to obtain data indicative of the respective pattern substantially free of effects caused by defects other than those caused by said reticle. The defects other than those caused by the reticle are identifiable as defects randomly appearing in the pattern-indicative data.

The test pattern may be produced on a test article, or on the article progressing on a production line (the so-called "production article"), or on the reference article. Generally speaking, the reference and test patterns are produced on the identical layer material areas, which may be areas of the same or different articles, and which may have a single material layer, or a multi-layer stack.

As indicated above, the data indicative of the pattern may be obtained using optical means (utilizing bright field or dark field inspection), optical critical dimension technique (e.g., scatterometry), or using inspection by a charged particles beam. Preferably, this data is indicative of the image of a pattern (at least one site thereof).

Generally, a pattern portion (site) having at least one pattern feature (die) is inspected (imaged) for the purposes of the reticle quality control. Preferably, however, in at least one of the reference and test patterns, a pattern portion including several pattern features (dies) is inspected. This enables to optimize the data to be free of defects other than those caused by the reticle. The data may be processed to correct the defective pattern feature, which can be implemented by dividing the defective pattern feature into image parts and replacing the defective image part by a corresponding image part of another pattern feature.

According to one embodiment of the invention, after producing the reference pattern, this pattern is inspected to obtain the first measured data indicative thereof, and this first measured data is stored to be used for the data analysis later on, when the current condition of the reticle is to be controlled. According to another embodiment of the invention, irrespectively of whether the first measured data has been obtained immediately after the production of the reference pattern or not, the reference pattern is stored and is inspected later on to provide the first measured data, when carrying out the control of the current condition of the reticle.

According to another broad aspect of the present invention, there is provided a method of controlling the condition of a reticle, the method comprising:

using said reticle when in a satisfied quality condition thereof to produce a reference pattern on an article, and using said reticle when in a current condition thereof a certain time period thereafter, to produce a test pattern on the identical article;

providing first measured data indicative of the reference pattern and providing a second measured data indicative of the test pattern, and analyzing the first and second measured data to generate output data indicative of the current condition of said reticle.

According to yet another broad aspect of the present invention, there is provided a method of controlling the condition of a reticle, the method comprising:

inspecting a reference pattern, produced on an article using the reticle to be controlled when considered to be of a satisfied condition, said inspecting comprising exposing at least a portion of the reference pattern to incident radiation and obtaining first measured data indicative of the radiation response of said at least portion of the pattern;

selectively controlling a current condition of said reticle a certain time period after the production of the reference pattern, said controlling comprising using said reticle to produce a test pattern on an identical article, exposing at least a portion of said test pattern to said incident radiation and obtaining second measured data indicative of the radiation response of said at least portion of the test pattern;

analyzing the first and second measured data to generate output data indicative of the current quality condition of said reticle.

According to yet another broad aspect of the present invention, there is provided a system for use in controlling the condition of a reticle, the system comprising:

(a) a measuring unit configured for irradiating at least a portion of a patterned article, detecting a radiation response of the sample, and obtaining measured data indicative thereof;

(b) a control unit configured for data communication with the measuring unit, so as to be responsive to the measured data indicative of the radiation response of the article corresponding to a current condition of said reticle, to analyze said measured data using certain reference data, and generate output data indicative of the data analysis results, said reference data being indicative of the radiation response of at least a portion of a reference pattern produced on an identical article using said reticle, when considered to be of a satisfied condition.

It should be understood that the term "measuring unit" used herein actually signifies any one of measuring, inspecting or metrology tool.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 1 is a schematic illustration of a system for carrying out a method of the present invention;

FIG. 2A shows the main steps in a method according to the invention;

FIG. 2B shows more specifically the operational steps of the method of the present invention.

DETAILED DESCRIPTION OF THE INVENTION

Figure 3A:
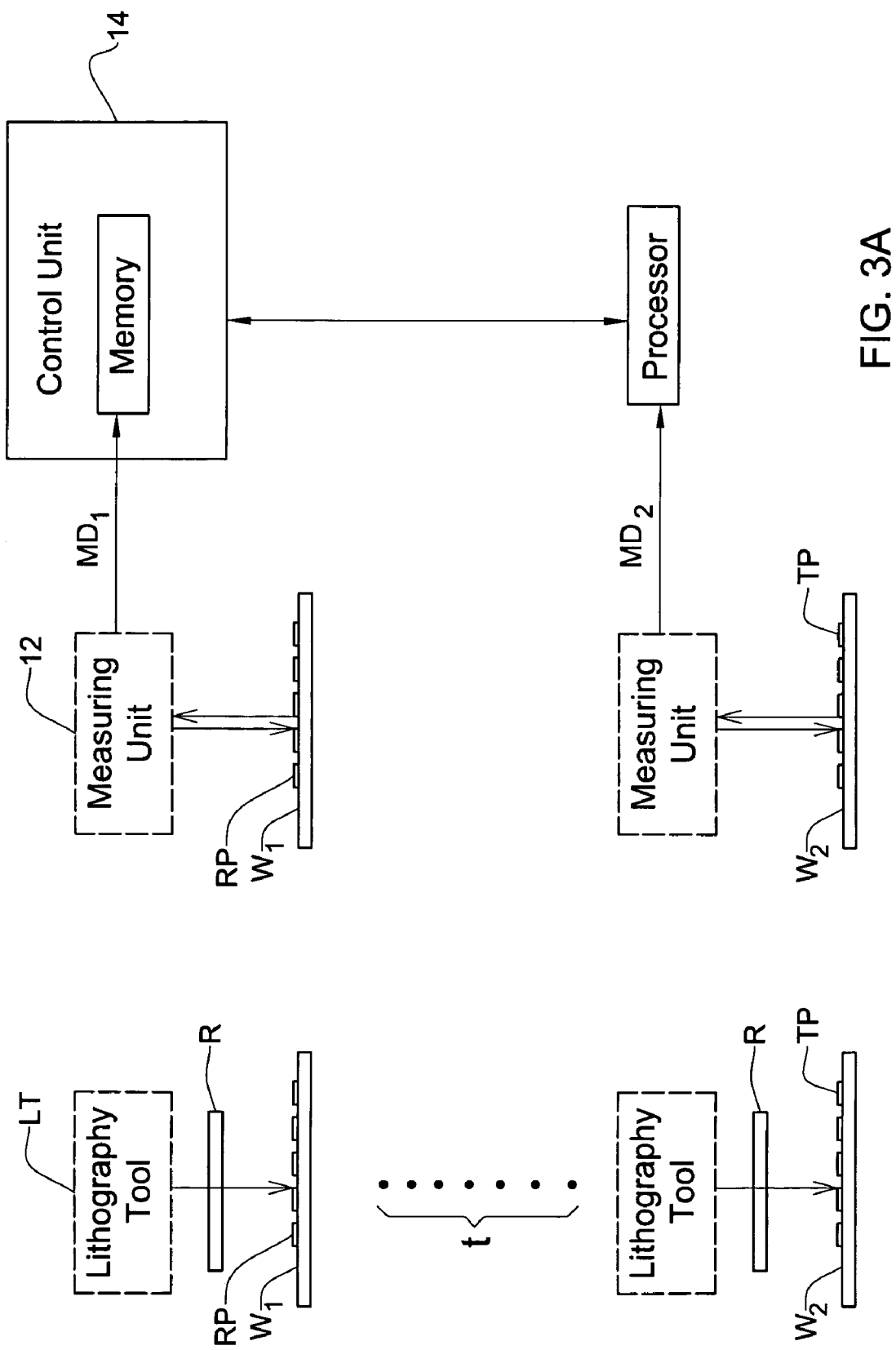
FIGS. 3A and 3B schematically illustrate two examples, respectively, of the technique of the present invention.

Referring to FIG. 1, there is illustrated a system 10 of the present invention for controlling the quality of a reticle that is used for patterning articles progressing on a production line. Such patterned articles may be flat panels, CD/DVD masters, etc. More specifically, the present invention is used for controlling semiconductor wafer manufacture and is therefore described below with reference to this specific application. It should, however, be understood that the principles of the present invention are not limited to this specific application.

The system 10 includes a measuring unit 12 (configured for measurements, inspection or metrology) and a control unit 14 connectable to the measuring unit via wires or wireless (e.g., via RF, IR or acoustic signal communication). The measuring unit 12 is configured for inspecting an article (wafer) to obtain measured data set indicative of at least a portion of the pattern. This measured data set is typically obtained by detecting a radiation response of the pattern to incident radiation. The measuring unit 12 thus includes a radiation source 12A, and a detector 12B for receiving a radiation response of the pattern and generating measured data indicative thereof, and may also include as its constructional part a support stage 12C for supporting the patterned article during measurements. Thus, the output of the measuring unit 12 is representative of the measured data indicative of the detected radiation response of the pattern, e.g., indicative of an image of the pattern. The construction and operation of the measuring unit 12 do not form part of the present invention and therefore need not be specifically described. The measured data indicative of a pattern may be obtained by any known suitable means, for example optical means operating in bright and/or dark field inspection mode or carrying out an optical critical dimension technique (e.g., scatterometry), or electronic means for charged particle beam imaging.

The control unit 14 is typically a computer system including inter alia a memory entity 14A, a data processing and analyzing entity 14B and a data presentation entity (monitor) 14C. The control unit 14 receives from the measuring unit 12 reference measured data $MD_1$ (constituting first data) indicative of an image of at least a portion of a reference pattern, and receives from the measuring unit 12 test measured data $MD_2$ (constituting second data) indicative of an image of at least a portion of a test pattern, and analyzes these data sets to generate output data indicative of the analysis results.

As shown in the figure in dashed lines, each of the reference pattern RP and test pattern TP is produced by applying a lithography tool LT utilizing the reticle R that is to be controlled. The reference pattern is produced on a reference or "golden" wafer $W_1$ by using a reticle to be controlled when in its initial satisfied-quality condition. The golden wafer $W_1$ has a layer material structure similar to that of the production wafers. As for the test pattern, it is produced in a test area, which may be located on another similar wafer $W_2$ (that may be a test wafer or the production wafer), or may be produced on a different area of the same reference wafer $W_1$. The test pattern is produced using the same reticle R after a certain period of time from the production of the reference pattern, during which the reticle R either has been in use or stored. This test pattern is inspected by the measuring unit 12 to obtain measured data $MD_2$ corresponding to the current condition of the reticle that is to be controlled.

As shown in FIG. 2A, controlling the current condition of the reticle R includes processing and analyzing the test measured data $MD_2$ indicative of the printed test pattern TP corresponding to the current condition of the reticle R and the reference measured data $MD_1$ indicative of the printed reference pattern RP corresponding to the initial satisfied-quality condition of the reticle R. These measured data sets $MD_1$ and $MD_2$ are compared to one another. The result is output data indicative of the current condition of the reticle, namely, at the time the test pattern TP was produced.

Preferably, the initially produced reference pattern is once imaged to obtain reference data $MD_1$, and this data is stored in the memory entity of the control unit (or on storage media (CD/DVD) or on the FAB server) to be further used for the analysis of the test measured data $MD_2$. Generally however, the reference pattern produced using the initial "perfect" reticle can be maintained, to be imaged later on to obtain data $MD_1$ when controlling the reticle's current condition is desired. This will be described further below with reference to FIGS. 3A and 3B.

Reference is now made to FIG. 2B showing more specifically the operational steps in the method of the invention for use in controlling the condition of a reticle that is to be sequentially applied for patterning wafers progressing on a production line.

First (reference) measured data $MD_1$ is provided, which is indicative of the image of a reference pattern (at least a portion thereof) produced by the reticle, when in "perfect" condition. As indicated above, the reference data $MD_1$ is obtained by applying measurements to the reference pattern on a reference article having a layer material structure similar to that of the production wafer, e.g., a single layer structure (the so-called "bare wafer"), or a multi-layer structure. It should be noted that instead of imaging the entire reference pattern, only part thereof may be imaged, preferably including multiple dies (but less that those of the entire wafer). This provides a significant population that may allow generating a "golden" die image that does not have defects, as will be described further below.

Second data $MD_2$ indicative of the image of a test pattern is provided. This test pattern is that produced by the same reticle after it has been in use or stored for a certain period of time. As indicated above, the test pattern may be printed on a different area of the reference article, on another wafer similar to the production one, or on the production wafer. In the first case, the reference article would undergo photoresist coating prior to creating thereon the test pattern, so as to protect the reference pattern from being affected by the etching process applied to the test area.

The first and second data sets are analyzed by comparing them to one another, and output data indicative of the current condition of the reticle is generated. The data analysis may utilize any known suitable image processing algorithm. As shown in the figure in dashed lines, optionally but preferably the following is carried out prior to this data analysis or as part of this data analysis. At least the first reference data undergoes image processing to obtain the so-called "combined image" of the reference pattern, which is free of effects caused by defects other than those caused by the reticle itself. Such defects other than those caused by the reticle are for example defects caused by the lithography process, which can therefore be identified as random defects, while defects caused by the reticle would periodically appear in the image. To this end, as indicated above, the imaging of multiple dies (but not necessarily the entire wafer) is carried out. Preferably, the reference and/or the test data is processed for correcting an image of a defective die. This is implemented by dividing the die image into several (generally, at least two) image parts, and then replacing the defective one of the image parts by the corresponding image part of another non-defective die.

Figure 3B:
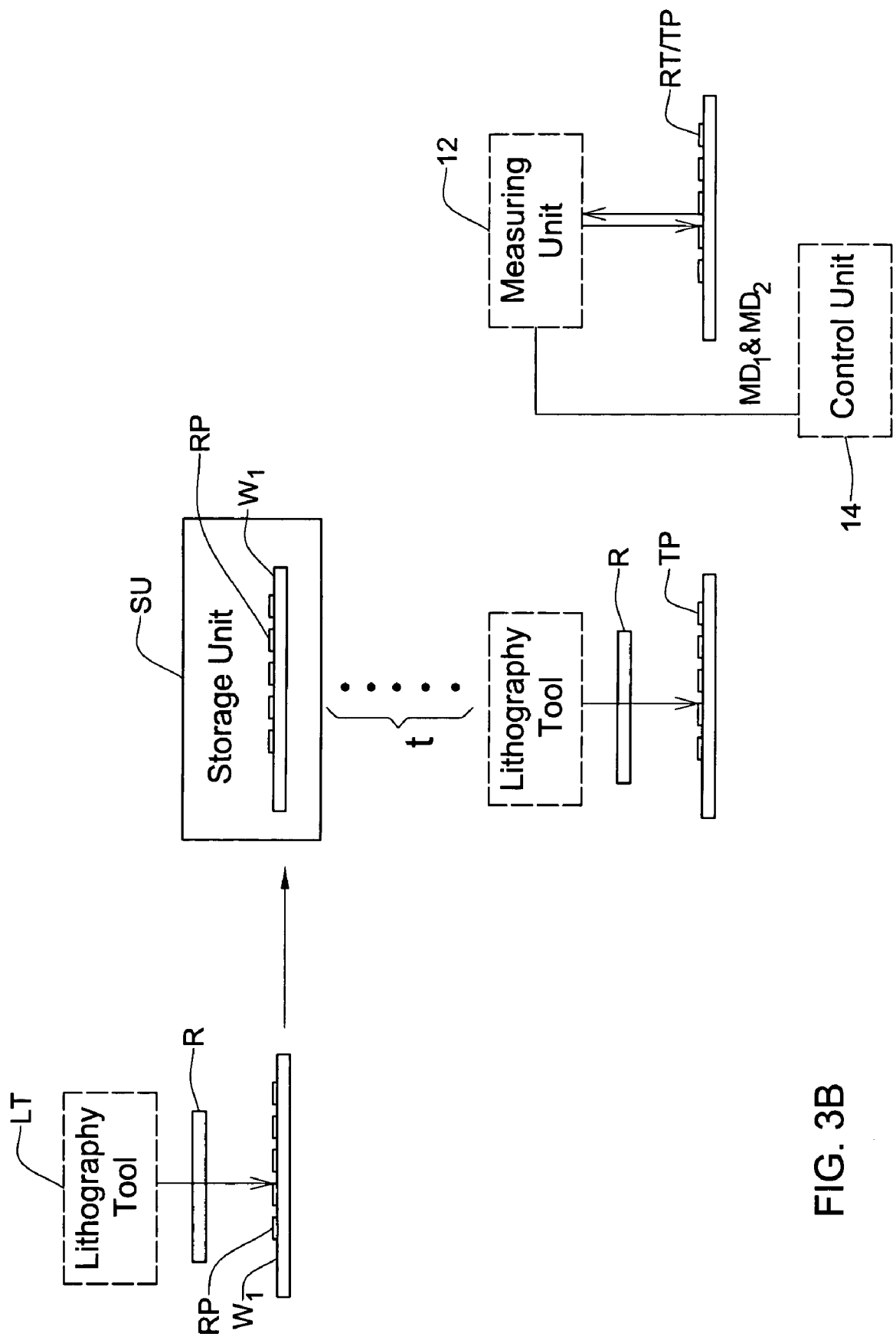

FIGS. 3A and 3B exemplify two different embodiments of the above-described method of the present invention.

In both examples, a reference pattern RP is created on a reference wafer $W_1$ (by a lithography tool LT) using a reticle R when in "perfect" condition. According to the example of FIG. 3A, upon creating the reference pattern RP, it is inspected (by measuring unit 12) and reference data $M_1$, indicative of the pattern image, is obtained. This reference data $M_1$ is stored in the control unit. The reticle R is then either stored, or is used for patterning (by lithography tool LT) production wafers, generally at $W_2$ having a layer material structure similar to that of the reference wafer $W_1$. After a certain time period t, when the current condition of the reticle R is to be controlled, the test data $MD_2$ is obtained by inspecting (by measuring unit 12) the production wafer $W_2$, or by producing and inspecting the test pattern on a similar test area (e.g., on a different area of the reference article). The test data $MD_2$ is supplied to the control unit where it is compared to the reference data $M_1$.

In the example of FIG. 3B, upon printing the reference pattern RP on a reference structure RS using a reticle R when in the "perfect" condition, this reference structure RS is kept in a storage unit SU under required environmental conditions. After the reticle R has been in use or has been stored (generally after a certain time period t) and its current condition is to be controlled, a test pattern TP is produced using this reticle (either on the production wafer $W_2$ or on another test area, which may and may not be on the reference wafer $W_1$). Then, measurements are applied to the reference pattern RP and to the test pattern TP to obtain the reference and test data $MD_1$ and $MD_2$, which are received and processed at the control unit as described above.

The technique present invention thus provides for controlling the condition of a reticle by directly detecting printing defects caused by the reticle itself. This is achieved by inspecting the results of printing on an article using this reticle.

Those skilled in the art will readily appreciate that various modifications and changes can be applied to the embodiments of the invention as hereinbefore described without departing form its scope defined in and by the appended claims.

The invention claimed is:

1. A method comprising: processing and analyzing test data obtained from at least a portion of a test pattern produced on an article using a reticle when in a current condition, and reference data obtained from at least a portion of a reference pattern previously produced on an identical reference article using said reticle when considered to be of a satisfied condition, and generating output data indicative of the current condition of said reticle.

2. The method of claim 1, wherein said processing and analyzing includes processing at least one of the reference and test data to obtain optimized data indicative of at least one of the reference pattern and the test pattern substantially free of effects caused by defects other than those caused by said reticle.

3. The method of claim 2, wherein said effects, caused by the defects other than those caused by the reticle, are identified as effects randomly appearing in the pattern-indicative data.

4. The method of claim 1, wherein said test pattern is produced on a test article having a layer material structure identical to that of the reference article.

5. The method of claim 1, wherein the reference pattern and the test pattern are produced on different areas of the same reference article.

6. The method of claim 1, wherein the reference pattern and the test pattern are produced in, respectively, reference and test areas each having a single-layer structure.

7. The method of claim 1, wherein the reference pattern and the test pattern are produced in, respectively, reference and test areas, each having a multi-layer stack structure.

8. The method of claim 1, wherein the data indicative of the pattern is obtained using bright field inspection of at least a portion of the pattern.

9. The method of claim 1, wherein the data indicative of the pattern is obtained using dark field inspection of at least a portion of the pattern.

10. The method of claim 1, wherein the data indicative of the pattern is obtained using inspection at least a portion of the pattern with a charged panicles beam.

11. The method of claim 1, wherein the data indicative of the pattern is obtained by applying optical critical dimension measurements to at least a portion of the pattern.

12. The method of claim 1, wherein the data indicative of the pattern includes several similar, periodically appearing, pattern features.

13. The method of claim 12, comprising applying image processing to the data indicative of the pattern to correct for defects in an image of the pattern feature.

14. The method of claim 13, wherein said correcting comprises dividing the image of the defective pattern feature into image pans and replacing the defective image pan by a corresponding image pan of an image of another pattern feature.

15. The method of claim 1, comprising, upon obtaining the reference data, storing the reference data to be used later for the data processing analyzing when controlling of the current condition of the reticle is needed.

16. The method of claim 1, comprising, upon producing the reference pattern, storing the reference pattern to be used later to provide said reference data when controlling of the current condition of the reticle is needed.

17. The method of claim 1, wherein the condition of the reticle is determined after an etching stage of a lithography process.

18. The method of claim 1, wherein the condition of the reticle is determined prior to carrying out an etching stage of a lithography process.

19. The method of claim 1, wherein the reticle is used for semiconductor wafers production.

20. The method of claim 19, wherein the test pattern is produced on a bare wafer.

21. The method of claim 19, wherein the test pattern is produced on a wafer having a layer material structure similar to that of the production wafer.

22. The method of claim 19, wherein said test pattern is produced on the production wafer.

23. The method of claim 19, wherein the data indicative of the pattern is indicative of an image of several dies on the wafer.

24. The method of claim 23, comprising die-to-die image processing.

25. The method of claim 23, comprising applying image processing to correct for defects in the die image.

26. The method of claim 25, wherein said correcting comprises dividing the image of the defective die into image parts and replacing the defective image part by a corresponding image part of another die image.

27. The method of claim 19, comprising, upon providing the reference data, storing said reference data to be used later on for the data processing and analyzing when controlling the current condition of the reticle is needed.

28. The method of claim 19, comprising, upon producing the reference pattern, storing said reference pattern to be used later on to provide said reference data when controlling the current condition of the reticle is needed.

29. A method comprising: using a reticle when in a satisfied quality condition thereof to produce a reference pattern on an article; using said reticle when in a current condition thereof a certain time period thereafter, to produce a test pattern on the identical article; providing first measured data indicative of the reference pattern and providing a second measured data indicative of the test pattern, and analyzing the first and second measured data to generate output data indicative of the current condition of said reticle.

30. A method comprising: inspecting a reference pattern, produced on an article using a reticle to be controlled when considered to be of a satisfied condition, said inspecting comprising exposing at least a portion of the reference pattern to incident radiation and obtaining first measured data indicative of a first radiation response of said at least a portion of the reference pattern; selectively controlling a current condition of said reticle a certain time period after the production of the reference pattern, said controlling comprising using said reticle to produce a test pattern on an identical article, exposing at least a portion of said test pattern to said incident radiation and obtaining second measured data indicative of a second radiation response of said at least a portion of the test pattern; analyzing the first and second measured data to generate output data indicative of the current condition of said reticle.

31. A system comprising: (a) a measuring unit configured for irradiating a sample test pattern produced on at least a portion of, an article by a reticle when in a current condition, detecting a radiation response of the sample test pattern, and obtaining measured data; resulting therefrom; (b) a control unit configured for data communication with the measuring unit, so as to be responsive to the measured data corresponding to the current condition of said reticle, to output results of an analysis of said measured data using reference data, said reference data resulting from a radiation response of at least a portion of a reference pattern produced on an identical article using said reticle, said reference pattern corresponding to a satisfied condition of said reticle.

32. A program storage device readable by machine, tangibly embodying a program of instructions executable by the machine to control a current condition of a reticle, according to a method comprising: processing and analyzing test data obtained from inspection of a test pattern, said test pattern produced on an article by the reticle when in the current condition, and reference data obtained from inspection of a reference pattern previously produced on an identical article by using said reticle, when said reticle is considered to be of a satisfied condition, and generating output data indicative of the current condition of said reticle.

33. A computer program product comprising a computer useable medium having computer readable program code embodied therein for controlling a current condition of a reticle, the computer program product comprising a data processing entity for processing and analyzing data obtained from inspection of a test pattern, produced by the reticle when in the current condition, on an article, and data obtained from inspection of a reference pattern previously produced on a similar article by using said reticle, when considered to be of a satisfied condition, and generating output data indicative of the current condition of said reticle.

* * * * *